United States Patent
Gatto et al.

(10) Patent No.: US 6,528,463 B1
(45) Date of Patent: *Mar. 4, 2003

(54) OIL SOLUBLE MOLYBDENUM COMPOSITIONS

(75) Inventors: Vincent James Gatto, Midlothian, VA (US); Carl A. Mike, Richmond, VA (US); John T. Loper, Richmond, VA (US)

(73) Assignee: Ethyl Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/533,229

(22) Filed: Mar. 23, 2000

(51) Int. Cl.[7] .................. C10M 159/18; C07F 11/00
(52) U.S. Cl. .................. 508/367; 508/362; 554/38; 554/71; 556/57
(58) Field of Search .................. 508/367; 554/38, 554/71; 556/57

(56) References Cited

U.S. PATENT DOCUMENTS

| | | |
|---|---|---|
| 3,121,059 A | 2/1964 | DeYoung et al. |
| 4,176,073 A | 11/1979 | Ryer et al. |
| 4,765,918 A | 8/1988 | Love et al. .................. 252/46.4 |
| 4,889,647 A * | 12/1989 | Rowan et al. .............. 508/367 |
| 5,137,647 A | 8/1992 | Karol ........................ 252/33.6 |
| 5,143,633 A | 9/1992 | Gallo et al. |
| 6,103,674 A * | 8/2000 | Nalesnik et al. ............. 508/334 |

FOREIGN PATENT DOCUMENTS

| | | |
|---|---|---|
| EP | 0546357 A1 | 6/1993 |
| EP | 0639578 A2 | 2/1995 |
| GB | 1085903 | 10/1967 |
| GB | 2053268 A | 2/1981 |
| GB | 2064548 A | 6/1981 |

* cited by examiner

Primary Examiner—Ellen M. McAvoy
(74) Attorney, Agent, or Firm—Dennis H. Rainear

(57) ABSTRACT

Organic molybdenum complexes comprising the reaction products of a long-chain mono carboxylic acid, a mono-alkylated alkylene diamine, glycerides, and a molybdenum source and their use as multifunctional additives for lubricating compositions.

50 Claims, No Drawings

OIL SOLUBLE MOLYBDENUM COMPOSITIONS

TECHNICAL FIELD

The present invention relates to novel organic molybdenum complexes and their use as multifunctional additives for lubricating compositions. The novel molybdenum compositions of the present invention comprise the reaction products of a long-chain monocarboxylic acid, a monoalkylated alkylene diamine, glycerides, and a molybdenum source.

BACKGROUND OF THE INVENTION

Lubricating oils for internal combustion engines of automobiles or trucks are subjected to a demanding environment during use. This environment results in the oil suffering oxidation that is catalyzed by the presence of impurities in the oil such as iron compounds and is also promoted by the elevated temperatures of the oil during use. This oxidation of lubricating oils during use is typically controlled to some extent by the use of antioxidant additives that may extend the useful life of the oil, particularly by reducing or preventing unacceptable viscosity increases.

Further, there have been many attempts to use lubricants to reduce the friction in an internal combustion engine so as to reduce the fuel consumption of the engine. Numerous classes of lubricant additives have been suggested for use as friction modifiers and to increase the energy efficiency provided to an engine by a lubricant.

Molybdenum containing additives are known to deliver a variety of beneficial properties to lubricants. Examples of lubricants that benefit from the addition of molybdenum are passenger car motor oils, natural gas engine oils, heavy-duty diesel oils, and railroad oils. Over the years molybdenum, when used properly, has been shown to deliver improved anti-wear protection, improved oxidation control, improved deposit control, and improved friction modification for fuel economy. There are many examples in the patent literature showing the use of molybdenum additives as antioxidants, deposit control additives, anti-wear additives and friction modifiers. A partial list of molybdenum-containing lubricant patents is provided below:

| | | | |
|---|---|---|---|
| U.S. Pat No. 5,840,672 | U.S. Pat No. 5,814,587 | U.S. Pat No. 4,529,526 | WO 95/07966 |
| U.S. Pat No. 5,650,381 | U.S. Pat No. 4,812,246 | U.S. Pat No. 5,458,807 | WO 95/07964 |
| U.S. Pat No. 5,880,073 | U.S. Pat No. 5,658,862 | U.S. Pat No. 5,696,065 | WO 95/07963 |
| U.S. Pat No. 5,665,684 | U.S. Pat No. 4,360,438 | U.S. Pat No. 5,736,491 | WO 95/27022 |
| U.S. Pat No. 5,786,307 | U.S. Pat No. 4,501,678 | U.S. Pat No. 5,688,748 | EP 0 447 916 A1 |
| U.S. Pat No. 5,807,813 | U.S. Pat No. 4,692,256 | U.S. Pat No. 5,605,880 | WO 95/07962 |
| U.S. Pat No. 5,837,657 | U.S. Pat No. 4,832,867 | U.S. Pat No. 4,705,641 | EP 0 768 366 A1 |

Numerous oil-soluble molybdenum compounds and their methods of preparation have been described in the art. For example, glycol molybdate complexes are described by Price et al. in U.S. Pat. No. 3,285,942; overbased alkali metal and alkaline earth metal sulfonates, phenates and salicylate compositions containing molybdenum are disclosed and claimed by Hunt et al in U.S. Pat. No. 4,832,857; molybdenum complexes prepared by reacting a fatty oil, a diethanolamine and a molybdenum source are described by Rowan et al in U.S. Pat. No. 4,889,647; a sulfur and phosphorus-free organomolybdenum complex of organic amide, such as molybdenum containing compounds prepared from fatty acids and 2-(2-aminoethyl) aminoethanol are taught by Karol in U.S. Pat. No. 5,137,647; overbased molybdenum complexes prepared from amines, diamines, alkoxylated amines, glycols and polyols are described by Gallo et al in U.S. Pat. No. 5,143,633; and 2,4-heteroatom substituted-molybdena-3,3-dioxacycloalkanes are described by Karol in U.S. Pat. No. 5,412,130.

Existing molybdenum technology, however, suffers from a number of problems that have limited its widespread use in lubricants. These problems include color, oil solubility, cost and corrosion.

Color—Many molybdenum technologies that appear in the patent literature deliver high levels of color when used even at moderate levels in crankcase oils. A non-discoloring molybdenum source is important because highly colored oils imply to the end consumer that the oil is "used" and therefore not capable of delivering the maximum amount of protection to the engine. When these highly colored molybdenum sources are used at low levels, e.g. 100–150 ppm delivered molybdenum as is typically required for oxidation, deposit and wear control, discoloration is not substantial but may still be visible. However, when these highly colored molybdenum compounds are used at high levels, e.g. 400–1000 ppm delivered molybdenum as is generally required for friction modification, discoloration is often significant. Traditionally, the color of fully formulated crankcase oils has been determined using the ASTM D 1500 color scale. Two types of unacceptable colors are possible. The first type of discoloration results in a dark rating on the D 1500 scale. The amount of acceptable finished lubricant darkening depends on the customer and application. There are no set standards for the amount of discoloration or darkening that is allowed. Generally, D 1500 ratings equal to or greater than 5.0 are considered unacceptable for a finished crankcase oil. Certain customers may find it difficult to market and sell such dark crankcase oils. The second type of discoloration produces "no match" on the D 1500 color scale. These finished lubricants, in addition to showing no match, are also very dark. Again, certain customers may find it difficult to market and sell such dark crankcase oils.

Oil Solubility—Many commercially available molybdenum additives designed for use in lubricants exhibit limited solubility in the finished lubricant product. For widespread use of a molybdenum product in lubricant applications the product must not only be soluble, at friction modifier treat levels, in the finished lubricant, it must also be soluble in the additive concentrates used to prepare the finished lubricant.

Cost—Molybdenum has long been viewed as an expensive additive for crankcase applications. Part of the reason for the high cost stems from the fact that many of the commercial molybdenum products have low levels, e.g. less than 5% by weight, of molybdenum in the additive. In some cases expensive organic ligands or expensive manufacturing processes are used to produce the commercial molybdenum compounds. There is a need for products with higher molybdenum contents that are prepared from lower cost raw materials.

Corrosion—Many molybdenum technologies that appear in the patent literature contain sulfur. The presence of sulfur in various crankcase applications is detrimental because certain types of sulfur are incompatible with elastomer seals and corrosive. Even the less aggressive forms of sulfur can be corrosive in very high temperature crankcase environments where significant amounts of oxygen and water are present. There are also trends to reduce the amount of sulfur present in finished crankcase lubricants. As these trends start to become a reality additives containing sulfur will become less desirable.

It is also well known that certain molybdenum containing friction modifiers function by a decomposition mechanism that results in the formation of a mixed molybdenum sulfide/molybdenum oxide layer on the metal surface of the engine. The molybdenum species that form on the metal surface can vary significantly and their composition is affected by the types of additives in the lubricant and the engine or test design. For example, it is known that molybdenum dithiocarbamates decompose when heated in use to produce products that include free amine and carbon disulfide. Both such products are aggressive towards copper that is present in the engine bearings. Furthermore, free amines are known to be aggressive towards certain types of elastomer seals present in a wide variety of engines. It is therefore desirable from a compatibility standpoint to develop new additives that are low in sulfur and free amines.

All of the above problems suggest a need for a molybdenum additive that has a high molybdenum content, low amine and sulfur content, good oil solubility, and non-discoloring to base oil and finished crankcase oils. It has unexpectedly been found that the molybdenum additives of the present invention provide the above benefits to lubricating compositions without the attendant problems commonly associated with molybdenum additives.

SUMMARY OF THE INVENTION

In one aspect, this invention is directed to molybdenum compositions that show excellent oil solubility and a low tendency to color finished crankcase oils. These molybdenum additives comprise the reaction products of a long-chain monocarboxylic acid, a mono-alkylated alkylene diamine, glycerides, and a molybdenum source.

In another embodiment, the present invention is directed to methods for improving the antioxidancy and friction properties of a lubricant by incorporating into the lubricant the novel molybdenum additives of the present invention.

DETAILED DESCRIPTION OF THE INVENTION

The molybdenum complexes of the present invention comprise the reaction products of a long-chain monocarboxylic acid, a mono-alkylated alkylene diamine, glycerides, and a molybdenum source.

The long-chain monocarboxylic acids suitable for use in the present invention preferably contain at least 8, and more preferably at least 12, carbon atoms. Examples of suitable acids for use in the present invention include fatty acids such as coconut acid, hydrogenated coconut acid, menhaden acid, hydrogenated menhaden acid, tallow acid, hydrogenated tallow acid, and soya acid. Additional long-chain carboxylic acids that may be used include lauric acid, myristic acid, palmitic acid, stearic acid, isostearic acid, arachidic acid, behenic acid, erucic acid, oleic acid, linoleic acid, and linolenic acid. Mixtures of acids may also be used and are sometimes preferred. For example, commercial oleic acid is actually a mixture of many fatty acids ranging in carbon chain length from 14 to 20.

The mono-substituted alkylene diamines suitable for use in the present invention are mono-alkylated and contain one secondary amine group and one primary amine group. Examples of some mono-alkylated alkylene diamines that may be used include methylaminopropylamine, methylaminoethylamine, butylaminopropylamine, butylaminoethylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyl-oxo-propyl-1,3-propanediamine, and octyl-oxo-propyl-1,3-propanediamine. Mono-alkylated alkylene diamines derived from fatty acids may also be used. Examples include N-coco alkyl-1,3-propanediamine (Duomeen™ C), N-tall oil alkyl-1,3-propanediamine (Duomeen™ T) and N-oleyl-1,3-propanediamine (Duomeen™ O), all commercially available from Akzo Nobel. Mixtures of mono-alkylated alkylene diamines may also be used.

Glycerides suitable for use in the present invention are of the formula:

wherein each R is independently selected from the group consisting of H and C(O)R' where R' may be a saturated or an unsaturated alkyl group having from 3 to 23 carbon atoms. Examples of glycerides that may be used include glycerol monolaurate, glycerol monomyristate, glycerol monopalmitate, glycerol monostearate, and monoglycerides derived from coconut acid, tallow acid, oleic acid, linoleic acid, and linolenic acids. Typical commercial monoglycerides contain substantial amounts of the corresponding diglycerides and triglycerides. These materials are not detrimental to the production of the molybdenum compounds, and may in fact be more active. Any ratio of mono- to di-glyceride may be used, however, it is preferred that from 30 to 70% of the available sites contain free hydroxyl groups (i.e., 30 to 70% of the total R groups of the glycerides represented by the above formula are hydrogen). A preferred glyceride is glycerol monooleate, which is generally a mixture of mono, di, and tri-glycerides derived from oleic acid, and glycerol. Suitable commercially-available glycerides include HiTEC® 7133 glycerol monooleate available from Ethyl Corporation which generally contains approximately 50% to 60% free hydroxyl groups.

Molybdenum Incorporation—The source of molybdenum is an oxygen-containing molybdenum compound capable of reacting with the reaction product of the fatty acid, the mono-substituted diamine and the glyceride. The sources of molybdenum include, among others, ammonium molybdate, sodium molybdate, molybdenum oxides and mixtures thereof. A particularly preferred molybdenum source comprises molybdenum trioxide.

The order of reacting the components of the present invention is not critical. The long-chain acid and the diamine may be reacted to form an aminoamide. The aminoamide is then reacted with the glyceride(s) and the molybdenum source. In one embodiment, the long-chain acid and the diamine can be reacted to form an ammonium carboxylate salt. The salt is then reacted with the glyceride(s) and the molybdenum source. In another embodiment, the long-chain acid and the diamine can be reacted to form a mixture of ammonium carboxylate salt and aminoamide. The salt/aminoamide mixture is then reacted with the glyceride(s) and the molybdenum source. In still another embodiment, the long-chain acid, the diamine, the molybdenum source and the glyceride(s) can all be charged to the reactor at one time (i.e., it is not necessary to pre-form the aminoamide or ammonium carboxylate).

The addition of water to these reactions is not required, however, water can facilitate the reaction rate and significantly improve the yields based on molybdenum incorporation. Water should be removed to drive the reaction to completion and maximize the amount of molybdenum incorporated.

The typical molar stoichiometry of the raw materials used to prepared these oil soluble molybdenum compounds is as follows:

| | |
|---|---|
| Long-chain acid | 1.0 |
| Mono-substituted alkylene diamine | 0.8 to 1.2 (based on the acid) |
| Glyceride mixture | 0.25 to 0.75 (based on the acid) |
| Molybdenum Source | 0.5 to 1.5 (based on acid) |
| Water | 0 to 100.0 (based on acid) |

An example of a preferred molar stoichiometry is as follows:

| | |
|---|---|
| Long-chain acid | 1.0 |
| Mono-substituted alkylene diamine | 1.0 |
| Glyceride mixture | 0.5 (approximate) |
| Molybdenum Source | 1.0 |
| Water | 5.0 |

The reaction between the long-chain acid and mono-alkylated diamine is typically carried out between 75 and 180° C. by combining the two materials and heating with mixing and under a nitrogen atmosphere. The preferred reaction temperature is between 100 and 150° C. Reaction times may vary, and typically range from 1 hour to 12 hours. A reaction solvent may be used as long as it does not react with the fatty oil or diamine. The preferred reaction solvents are toluene, xylenes, heptane, and various naphthenic, paraffinic and synthetic diluent oils. The amount of solvent used is not critical but is kept to a minimum for practical purposes. In general, when the reaction times are short and/or when the reaction temperatures are low, the ammonium carboxylate salts are the principal products formed. At higher temperatures and longer reaction times larger quantities of the aminoamide products are formed. Water removal facilitates the formation of the aminoamide products.

An example of a suitable method of molybdenum incorporation is as follows: Molybdenum trioxide, the glyceride (s) and water are added to the aminoamide/ammonium carboxylate reaction mass maintained at approximately 60–80° C. The amount of water used is generally equivalent to the amount of molybdenum trioxide used, by weight, but higher levels of water may be used. After addition of the molybdenum trioxide, the glyceride(s) and water, the reaction is slowly heated to reflux temperature with gradual removal of water. Water may be removed by distillation, vacuum distillation, or by azeotropic distillation from a suitable solvent. Suitable solvents include toluene, xylenes, and heptane. The reaction can be monitored by removal of water. The amount of water collected is equal to the amount added plus the amount generated to produce the molybdenum complex. The reaction generally requires 1 to 10 hours. At the end of the reaction period the mixture is cooled, filtered to remove any unreacted molybdenum trioxide and, if used, the solvent is removed by vacuum distillation. In many cases filtration is not required because all of the molybdenum trioxide is reacted. From a practical and cost standpoint, it is desirable to react all of the molybdenum trioxide. The product prepared by this process is a dark amber wax or viscous liquid.

The molybdenum complexes of the present invention are oil-soluble molybdenum compounds substantially free of reactive sulfur. As used herein the term "oil-soluble molybdenum compound substantially free of reactive sulfur" means any molybdenum compound that is soluble in the lubricant or formulated lubricant package and is substantially free of reactive sulfur. The term reactive sulfur is sometimes referred to as divalent sulfur or oxidizable sulfur. Reactive sulfur also includes free sulfur, labile sulfur or elemental sulfur, all of which are sometimes referred to as "active" sulfur. Active sulfur is sometimes referred to in terms of the detrimental effects it produces. These detrimental effects include corrosion and elastomer seal incompatibility. As a result, "active" sulfur is also referred to as "corrosive sulfur" or "seal incompatible sulfur". The forms of reactive sulfur that contain free, or "active" sulfur, are much more corrosive to engine parts than reactive sulfur that is very low in free or "active" sulfur. At high temperatures and under severe conditions, even the less corrosive forms of reactive sulfur can cause corrosion. It is therefore desirable to have a molybdenum compound that is substantially free of all reactive sulfur, active or less active. By "soluble" or "oil-soluble" it is meant that the molybdenum compound is oil-soluble or capable of being solubilized under normal blending or use conditions into the lubrication oil or diluent for the concentrate. By "substantially free" it is meant that trace levels of sulfur may be present due to impurities or catalysts left behind from the manufacturing process. This sulfur is not part of the molybdenum compound itself, but is left behind from the preparation of the molybdenum compound. Such impurities can sometimes deliver as much as 0.05 weight percent of sulfur to the final molybdenum product.

As discussed previously, in many cases it is desirable to have an additive low in free amines in order to avoid copper corrosion and potential problems with elastomer seals. In one embodiment of the present invention, the novel molybdenum compounds have a ratio (wt/wt) of nitrogen to molybdenum (N/Mo) of $\leq 0.6$, preferably $\leq 0.4$ and more preferably $\leq 0.3$.

The molybdenum additives of the present invention may be used as antioxidants, deposit control additives, anti-wear additives and/or friction modifiers. The treat rates of the molybdenum additives depend upon the desired finished lubricant properties, however, typically the additives are present in an amount so as to provide at least about 50 ppm, and preferably from about 50 to about 1000 ppm, of molybdenum to the finished lubricant. The concentration of molybdenum in the lubricants according to the invention has no particular upper limit, however, for economic reasons a maximum level of about 1000 ppm is generally preferred although not required.

The molybdenum complexes of the present invention have excellent solubility in a wide variety of basestock types and have a reduced tendency to color finished crankcase oils. Further, the complexes have high molybdenum incorporations, may be prepared from low cost raw materials and have straightforward production processes.

The composition of the lubricant oil can vary significantly based on the customer and specific application. The oil will typically contain, in addition to the molybdenum compounds of the invention, a detergent/inhibitor additive package and a viscosity index improver. In general, the lubricant oil is a formulated oil which is composed of between 65 and 95 weight percent (wt. %) of a base oil of lubricating viscosity, between 0 and 30 wt. % of a polymeric viscosity index improver, between about 5 and 15 wt. % of an additional additive package and typically a sufficient amount of molybdenum complex to provide at least about 50 ppm of molybdenum to the finished lubricant.

The detergent/inhibitor additive package may include dispersants, detergents, zinc dihydrocarbyl dithiophosphates (ZDDP), additional antioxidants, pour point depressants, corrosion inhibitors, rust inhibitors, foam inhibitors and supplemental friction modifiers.

The dispersants are nonmetallic additives containing nitrogen or oxygen polar groups attached to a high molecular weight hydrocarbon chain. The hydrocarbon chain provides solubility in the hydrocarbon base stocks. The dispersant functions to keep oil degradation products suspended in the oil. Examples of commonly used dispersants include hydrocarbyl-substituted succinimides, hydrocarbyl amines, polyhydroxy succinic esters, hydrocarbyl-substituted Mannich bases, and hydrocarbyl-substituted triazoles. Generally, the dispersant is present in the finished oil in an amount between 0 and 10 wt. %.

The detergents are metallic additives containing charged polar groups, such as phenates, sulfonates or carboxylates, with aliphatic, cycloaliphatic, or alkylaromatic chains, and several metal ions. The detergents function by lifting deposits from the various surfaces of the engine. Examples of commonly used detergents include neutral and overbased alkali and alkaline earth metal sulfonates, overbased alkaline earth salicylates, phosphonates, thiopyrophosphonates, and thiophosphonates. Generally, when used, the detergents are present in the finished oil in an amount from about 0.5 to 5.0 wt. %.

The ZDDP's are the most commonly used antiwear additives in formulated lubricants. These additives function by reacting with the metal surface to form a new surface active compound which itself is deformed and thus protects the original engine surface. Other examples of anti-wear additives include tricresol phosphate, dilauryl phosphate, sulfurized terpenes and sulfurized fats. The ZDDP also functions as an antioxidant. Generally, the ZDDP is present in the finished oil between about 0.25 and 1.5 wt. %. It is desirable from environmental concerns to have lower levels of ZDDP. Phosphorus-free oils contain no ZDDP.

The inclusion of the present molybdenum compounds generally removes the need for supplemental antioxidants. However, a supplementary antioxidant may be included in oils that are less oxidatively stable or in oils that are subjected to unusually severe conditions. The amount of supplemental antioxidant will vary depending on the oxidative stability of the base stock. Typical treat levels in finished oils can vary from 0 to 2.5 wt %. The supplementary antioxidants that are generally used include diarylamines, hindered phenols, hindered bisphenols, sulfurized phenols, sulfurized olefins, alkyl sulfides and polysulfides, dialkyl dithiocarbamates, and phenothiazines.

The base oil according to the present invention may be selected from any of the synthetic or natural oils or mixtures thereof. These oils are typical crankcase lubrication oils for spark-ignited and compression-ignited internal combustion engines, for example natural gas engines, automobile and truck engines, marine, and railroad diesel engines. The synthetic base oils include alkyl esters of dicarboxylic acids, polyglycols and alcohols, poly-alpha-olefins, including polybutenes, alkyl benzenes, organic esters of phosphoric acids, and polysilicone oils. Natural base oils include mineral lubrication oils that may vary widely as to their crude source, e.g., as to whether they are paraffinic, naphthenic, or mixed paraffinic-naphthenic. The base oil typically has a viscosity of about 2 to about 15 cSt and preferably about 2.5 to about 11 cSt at 100° C.

The lubricating oil compositions of this invention can be made by adding the molybdenum compound, and any supplemental additives, to an oil of lubricating viscosity. The method or order of component addition is not critical. Alternatively, the molybdenum compounds, along with any additional additives, can be added to the oil as a concentrate.

The lubricating oil concentrate will typically comprise a solvent and from about 2.5 to 90 wt. % and preferably 5 to 75 wt. % of the combination of the molybdenum compound of this invention and the optional supplemental additives. Preferably the concentrate comprises at least 25 wt. % and most preferably at least 50 wt. % of the combination of molybdenum compound and supplemental additives.

In one embodiment, the present invention is directed to a method of improving the oxidation stability of a lubricating oil, wherein said method comprises adding to a lubricating oil an oxidation stability improving amount of the molybdenum complexes of the present invention, wherein said oxidation stability improving amount of said molybdenum complex is effective to improve the oxidative stability of the lubricating oil, as compared to the same lubricating oil except that it is devoid of said molybdenum complex. For improving the oxidation stability of the oil, the molybdenum complex is typically present in the lubricating oil in an amount sufficient to provide at least 50 ppm, preferably at least 100 ppm and more preferably at least 150 ppm, of molybdenum to the finished lubricating oil.

In one embodiment, the present invention is directed to a method of improving the fuel economy of an internal combustion engine, wherein said method comprises using as the crankcase lubricating oil for said internal combustion engine a lubricating oil containing the molybdenum complexes of the present invention, wherein said molybdenum complex is present in an amount sufficient to improve the fuel economy of the internal combustion engine using said crankcase lubricating oil, as compared to said engine operated in the same manner and using the same crankcase lubricating oil except that the oil is devoid of said molybdenum complex. For improving fuel economy, the molybdenum complex is typically present in the lubricating oil in an amount sufficient to provide at least 150 ppm, preferably at least 400 ppm and more preferably at least 800 ppm, of molybdenum to the finished lubricating oil.

In one embodiment, the present invention is directed to a method of reducing deposits in an internal combustion engine, wherein said method comprises using as the crankcase lubricating oil for said internal combustion engine a lubricating oil containing the molybdenum complexes of the present invention, wherein said molybdenum complex is present in an amount sufficient to reduce the weight of deposits in an internal combustion engine operated using said crankcase lubricating oil, as compared to the weight of deposits in said engine operated in the same manner and using the same crankcase lubricating oil except that the oil is devoid of said molybdenum complex. For reducing deposits, the molybdenum complex is typically present in the lubricating oil in an amount sufficient to provide at least 50 ppm, preferably at least 100 ppm and more preferably at least 150 ppm, of molybdenum to the finished lubricating oil. Representative of the deposits that may be reduced using the compositions of the present invention include piston deposits, ring land deposits, crown land deposits and top land deposits.

In one embodiment, the present invention is directed to a method of reducing wear in an internal combustion engine, wherein said method comprises using as the crankcase lubricating oil for said internal combustion engine a lubricating oil containing the molybdenum complexes of the present invention, wherein said molybdenum complex is present in an amount sufficient to reduce the wear in an internal combustion engine operated using said crankcase lubricating oil, as compared to the wear in said engine operated in the same manner and using the same crankcase lubricating oil except that the oil is devoid of said molybdenum complex. For reducing wear, the molybdenum complex is typically present in the lubricating oil in an amount sufficient to provide at least 50 ppm, preferably at least 100 ppm and more preferably at least 150 ppm, of molybdenum to the finished lubricating oil. Representative of the types of wear that may be reduced using the compositions of the present invention include cam wear and lifter wear.

The following examples are illustrative of the invention and its advantageous properties and are not intended to be limiting. In these examples as well as elsewhere in this application, all parts and percentages are by weight unless otherwise indicated.

EXAMPLES

The general synthetic method for preparation of the molybdenum compounds in the following Examples involves first preparing an aminoamide/ammonium carboxylate mixture followed by the molybdenum incorporation step. In all procedures a four-neck reaction flask was equipped with a stirrer, a thermometer, a reflux condenser, and a nitrogen inlet. Dry nitrogen was passed into the reactor through the inlet and out of the reactor through the reflux condenser. The quantities of reagents used in each reaction are provided in Table 1. The mono-substituted alkylene amine (Duomeen™ C) was charged to the flask and heated with mixing to approximately 100° C. The long-chain acid (oleic acid) was slowly added to the amine while maintaining the reaction temperature at 100° C. The remaining procedures for each of the samples were as follows:

M.1C (control without glyceride(s))—After the addition of the acid the mixture was heated for 2 hours at 150° C. Xylenes were added and the generated water removed by azeotropic distillation, via a dean-stark trap, over a 2 hour period. The reaction was cooled to 80–85° C. and the molybdenum trioxide and water were added. The reaction was mixed vigorously and brought to reflux temperature. Water was removed azeotropically over a 2 hour period.

M.2—After the addition of the acid the mixture was heated for 2 hours at 160° C. Xylenes were added and the generated water removed by azeotropic distillation, via a dean-stark trap, over a 2 hour period. The reaction was cooled to 80–85° C. and the molybdenum trioxide, glycerol monooleate (HiTEC®7133 additive from Ethyl Corporation), and water were added. The reaction was mixed vigorously and brought to reflux temperature. Water was removed azeotropically over a 3 hour period.

M.3—This procedure was identical to M.2 with the only change being the amount of molybdenum trioxide added.

M.4—This procedure was identical to M.2 with the only differences being the amount of molybdenum trioxide added and a 2 hour reaction period for the molybdenum incorporation step.

M.5—This procedure was identical to M.2 with the only differences being the amount of molybdenum trioxide added and the amount of glycerol monooleate (HiTEC®7133 additive) added.

M.6—After the addition of the acid the mixture was heated for 2 hours at 160° C. A paraffinic process oil diluent was then added. The reaction was cooled to 80–85° C. and the molybdenum trioxide, glycerol monooleate (HiTEC®7133 additive), toluene, and water were added. The reaction was mixed vigorously and brought to reflux temperature. Water was removed azeotropically, via a dean-stark trap, over a 3 hour period.

M.7—This procedure was identical to M.6 with the only difference being the addition of the paraffinic process oil diluent at the end of the molybdenum incorporation reaction.

M.8—This procedure was identical to M.7 with the only differences being the amount of glycerol monooleate used (HiTEC®7133 additive) and the amount of paraffinic process diluent oil used.

M.9—This procedure was identical to M.7 with the only differences being the amount of molybdenum trioxide used and the amount of paraffinic process oil diluent used.

M.10C—(control without aminoamide/ammonium carboxylate intermediate)—This procedure was performed in the absence of the aminoamide/ammonium carboxylate intermediate mixture. The flask was initially charged with glycerol monooleate (HiTEC®7133 additive) and xylenes and heated to 85° C. with vigorous mixing. Molybdenum trioxide and water were added and the reaction mixture brought to reflux temperature. Water was removed azeotropically over a 3 hour period.

After the molybdenum incorporation steps the reaction mixtures were cooled to approximately 50–60° C. and filtered. The filtrate was concentrated on a rotary evaporator until all the solvent was removed.

TABLE 1

Preparation of molybdenum compounds

| Sample | Oleic Acid (g) | Amine (g) | Glyceride (g) | Solvent | $MoO_3$ (g) | Water (g) | Diluent (g) |
|---|---|---|---|---|---|---|---|
| M.1C* | 42.4 | 37.5 | 0 | 75 mL Xylenes | 10.8 | 12.5 | 0 |
| M.2 | 33.8 | 30.0 | 21.4 | 50 mL Xylenes | 8.7 | 10.0 | 0 |
| M.3 | 33.8 | 30.0 | 21.4 | 50 mL Xylenes | 13.0 | 10.0 | 0 |
| M.4 | 33.8 | 30.0 | 21.4 | 50 mL Xylenes | 17.3 | 10.0 | 0 |

TABLE 1-continued

Preparation of molybdenum compounds

| Sample | Oleic Acid (g) | Amine (g) | Glyceride (g) | Solvent | $MoO_3$ (g) | Water (g) | Diluent (g) |
|---|---|---|---|---|---|---|---|
| M.5 | 33.8 | 30.0 | 32.1 | 50 mL Xylenes | 21.6 | 10.0 | 0 |
| M.6 | 33.8 | 30.0 | 21.4 | 50 mL Toluene | 17.4 | 10.0 | 42.0 |
| M.7 | 33.8 | 30.0 | 21.4 | 50 mL Toluene | 17.4 | 10.0 | 42.0 |
| M.8 | 33.8 | 30.0 | 25.6 | 50 mL Toluene | 17.3 | 10.0 | 34.0 |
| M.9 | 33.8 | 30.0 | 21.4 | 50 mL Toluene | 15.1 | 10.0 | 25.0 |
| M.10C* | 0 | 0 | 53.7 | 50 mL Xylenes | 10.8 | 10.0 | 0 |

*Comparative examples

Table 2 sets forth various reaction products in terms of their viscosities, TBN, nitrogen content and molybdenum content.

TABLE 2

Properties of molybdenum compounds

| Sample | Wt. % Diluent | Viscosity @ 100° C. | TBN mg KOH/g | Wt. % Nitrogen | Wt. % Molybdenum | N/Mo |
|---|---|---|---|---|---|---|
| M.1C* | 0 | 84.1 | 73.0 | 4.3 | 7.6 | 0.57 |
| M.2 | 0 | 37.9 | 50.6 | 3.5 | 6.1 | 0.57 |
| M.3 | 0 | 92.4 | 45.7 | 3.4 | 8.5 | 0.40 |
| M.4 | 0 | 187.2 | 41.3 | 3.2 | 10.7 | 0.30 |
| M.5 | 0 | 265.6 | 32.8 | 2.8 | 11.8 | 0.24 |
| M.6 | 30 | 40.8 | 29.8 | 2.3 | 7.3 | 0.32 |
| M.7 | 30 | 46.8 | 30.0 | 2.4 | 7.8 | 0.31 |
| M.8 | 25 | 76.5 | 30.5 | 2.4 | 7.9 | 0.30 |
| M.9 | 21 | 79.1 | 36.8 | 2.7 | 7.7 | 0.35 |
| M.10C* | 0 | 19.6 | 0.1 | 0 | 0.3 | 0 |

*Comparative examples

The color and a visual solubility check was determined for the molybdenum compounds using a fully-formulated 5W-30 passenger car motor oil (PCMO) as well as a paraffinic process oil diluent. The color method was ASTM D1500. Color results are reported to the nearest one-half unit match on the D1500 color scale. The treat levels in Table 3 are based on the amount (weight percent) of molybdenum compound added to the oil, not the amount of molybdenum delivered to the oil.

TABLE 3

Aesthetic Properties

| Molybdenum type | Solubility in PO #5 | Color in PO #5 (1 wt. % treat) | Solubility in PCMO | Color in PCMO (1 wt. % treat) | Color in PCMO (0.5 wt. % treat) |
|---|---|---|---|---|---|
| M.1C* | Hazy | 2.5 | Soluble | No Match | No Match |
| M.2 | Soluble | 1.5 | Soluble | 3.5 | 3.5 |
| M.3 | Soluble | 2.0 | Soluble | 4.5 | 3.5 |
| M.4 | Soluble | 2.0 | Soluble | No Match | 4.0 |
| M.5 | Soluble | No Match | Soluble | No Match | 4.0 |
| M.6 | Hazy | 1.0 | Soluble | 3.5 | 3.5 |
| M.7 | Soluble | 1.0 | Soluble | 3.5 | 3.0 |
| M.8 | Soluble | 1.0 | Soluble | 3.5 | 3.0 |
| M.9 | Soluble | 1.5 | Soluble | 3.5 | 3.0 |
| M.10C* | Soluble | 0.5 | Soluble | 3.0 | 3.0 |

*Comparative examples

It is clear, from an examination of Table 3, that the molybdenum compounds of the present invention gave exceptionally low colors at friction modifier treat levels in process oil and finished PCMO. The control with no glyceride(s), M.1C, produced darker or oddly colored oils that showed no match in a fully formulated PCMO on the ASTM D 1500 scale. The control with no aminoamide/ammonium carboxylate mixture, M.10C, contained very low levels of molybdenum due to the ineffectiveness of the aminoamide/ammonium carboxylate-free reaction system to incorporate molybdenum. Commercial oil soluble molybdenum compounds generally contain between 4 and 8 weight % molybdenum. Levels lower than 4% are viewed as impractical because of the high treat levels required to deliver friction modifier levels of molybdenum to fully formulated crankcase oils. Samples of the present invention, M.2, M.3, M.7, M.8, and M.9, contained high levels of molybdenum and produced acceptable colors in fully formulated PCMO on the D 1500 scale. Samples of the present invention, M.4, M.5, and M.6, showed some negative attributes in terms of color and solubility but these materials were still more acceptable than the controls and also contained higher molybdenum contents. Note that samples M.4 and M.5 contain very high levels of molybdenum. No color match with these materials at high treat levels is not a significant concern since these materials could be used at lower treat levels to deliver the required amount of molybdenum. In addition, sample M.5 has a very low ratio of nitrogen to molybdenum. This translates to a very low level of potential free amines that would form from decomposition on the metal surface.

The antioxidant performance of the molybdenum additives in a PCMO was determined using pressurized differential scanning calorimetry (PDSC). Test oils were prepared by adding the molybdenum additives, as described in Table 1, to a pre-blend oil. The pre-blend oils (PCMO A and PCMO B) contained a viscosity index improver, a dispersant, detergents, ZDDP, supplemental antioxidants and base oil, in concentrations typically found in fully formulated multi-grade passenger car motor oils.

The PDSC procedure used is described by J. A. Walker and W. Tsang in "Characterization of Lubrication Oils by Differential Scanning Calorimetry", SAE Technical Paper Series, 801383 (Oct. 20–23, 1980). Oil samples were treated with an iron naphthenate catalyst (50 ppm Fe) and approximately 2 milligrams were analyzed in an open aluminum hermetic pan. The DSC cell was pressurized with 400 psi of air containing approximately 55 ppm $NO_2$ as an oxidation catalyst. The temperature ramping method was used wherein the temperature is ramped at 2.5° C. per minute up to 250° C. During the temperature ramping sequence an exothermic release of heat is observed. This exothermic release of heat marks the oxidation reaction. The temperature at which the exothermic release of heat is observed is called the oxidation onset temperature and is a measure of the oxidative stability of the oil (i.e., the higher the oxidation onset temperature the greater the oxidative stability of the oil). All oils were evaluated in multiple runs and the results averaged. The base lubricant, the molybdenum content of the finished lubricant and the PDSC results are set forth in Table 4.

TABLE 4

PDSC Results

| Oil # | Base lubricant | Molybdenum type | Amount of molybdenum in the finished oil (ppm Mo) | Onset Temperature (° C.) |
|---|---|---|---|---|
| 1* | PCMO A | — | 0 | 205.6 |
| 2 | A | M.2 | 150 | 213.0 |
| 3 | A | M.2 | 400 | 216.2 |
| 4 | A | M.2 | 600 | 220.4 |
| 5 | A | M.3 | 150 | 214.4 |
| 6 | A | M.3 | 400 | 217.9 |
| 7 | A | M.3 | 600 | 219.0 |
| 8 | A | M.4 | 150 | 215.7 |
| 9 | A | M.4 | 400 | 215.9 |
| 10 | A | M.4 | 600 | 219.0 |
| 11 | PCMO B | — | 0 | 208.7 |
| 12 | B | M.2 | 150 | 215.7 |
| 13 | B | M.2 | 400 | 214.6 |
| 14 | B | M.2 | 600 | 218.4 |
| 15 | B | M.3 | 150 | 216.7 |
| 16 | B | M.3 | 400 | 216.0 |
| 17 | B | M.3 | 600 | 215.1 |
| 18 | B | M.4 | 150 | 215.3 |
| 19 | B | M.4 | 400 | 216.6 |
| 20 | B | M.4 | 600 | 216.3 |

*Comparative examples

The onset temperature results in Table 4 clearly show the efficacy of the molybdenum compounds according to the invention (Oils #2–10 and 12–20) in controlling oxidation in fully formulated passenger car motor oils.

The deposit control performance of the molybdenum additives in a fully formulated PCMO was determined using the Caterpillar Modified Micro-Oxidation Test (CMOT). The CMOT is a commonly used technique for evaluating the deposit forming tendencies of a wide variety of passenger car and diesel lubricants as well as mineral and synthetic basestocks. The test measures the oxidative stability and deposit forming tendencies of lubricants under high temperature thin-film oxidation conditions.

In the CMOT, a thin-film of oil is placed in a weighed indented low carbon steel sample holder immersed in a test tube that is placed in a high temperature bath. Dry air is passed, at a specific rate, through the test tube, over the oil sample, and out of the test tube to the atmosphere. At specific time intervals the carbon steel sample holders are removed from the high temperature bath, rinsed with solvent to remove any remaining oil, and oven dried. The sample holders are weighed to determine the amount of deposit formed at the sampling interval. The method requires sampling at a variety of time intervals and determining percent deposits at each time interval. The CMOT tests were run using a temperature of 220° C., an air flow of 20 cc/min and sampling times of 90, 120, 150 and 180 minutes. All of the molybdenum compounds were present in the oils so as to provide 150 ppm of molybdenum to the finished lubricant.

The weight % Deposits at different sampling times are set forth in Table 5.

TABLE 5

CMOT Results

| Oil # | Base lubricant | Molybdenum type | 90 Min. | 120 Min. | 150 Min. | 180 Min. |
|---|---|---|---|---|---|---|
| 1* | PCMO A | none | 3.7 | 10.0 | 8.8 | 16.6 |
| 2 | A | M.2 | 1.5 | 1.0 | 1.2 | 1.3 |
| 3 | A | M.3 | 0.7 | 1.8 | 6.4 | 0.9 |
| 4 | A | M.4 | 0.4 | 1.1 | 2.1 | 1.9 |
| 5* | PCMO B | None | 19.6 | 19.6 | 24.8 | 24.7 |
| 6 | B | M.2 | 0.8 | 7.3 | 12.5 | 20.1 |
| 7 | B | M.3 | 1.1 | 3.4 | 16.1 | 19.8 |
| 8 | B | M.4 | 1.1 | 18.2 | 22.0 | 22.6 |

*Comparative examples

The results presented in Table 5 clearly indicate that the additive components according to the invention (Oils #2–4 and 6–8) provide improved deposit control in the CMOT as evidenced by the lower amount of deposit formation compared to the molybdenum-free lubricant.

Boundary lubrication occurs when fluid films are thin enough that opposing metal surfaces interact with one another. When this interaction occurs, friction increases. In an engine, an increase in friction results in a decrease in fuel economy.

The boundary friction coefficient of the molybdenum additives in a fully formulated PCMO was determined using a High Frequency Reciprocating Rig (HFRR). The HFRR operates by oscillating a ball across a plate in a sample cell containing 1–2 ml of sample. The frequency of oscillation, path length that the ball travels, load applied to the ball and test temperature can be controlled. By controlling these parameters, the boundary frictional properties of a fluid can be assessed.

The molybdenum additives of the present invention were added to a pre-blend oil contained a viscosity index improver, a dispersant, detergents, ZDDP, supplemental antioxidants and baseoil, in concentrations typically found in fully formulated multi-grade passenger car motor oils. The boundary frictional properties of these fluids were assessed using an HFRR under the same conditions described in "Predicting Seq. VI and VIA Fuel Economy from Laboratory Bench Tests" by C. Bovington, V. Anghel and H. A. Spikes (SAE Technical Paper 961142), that is, 4N load, 1 mm path length, 20 Hz frequency. The frictional properties were measured at 130° C.

Table 6 demonstrates the improvements in boundary friction results obtained by the addition of the novel molybdenum additives of the present invention to motor oils as compared to motor oils containing no molybdenum. Lower boundary friction results are indicative of improved fuel economy.

TABLE 6

Boundary Friction Results

| Oil # | Molybdenum type | Amount of molybdenum in the finished oil (ppm Mo) | Boundary Friction Coefficient |
|---|---|---|---|
| 1* | None | — | 0.130 |
| 2 | M.1 | 150 | 0.119 |
| 3 | M.1 | 400 | 0.102 |
| 4 | M.1 | 600 | 0.099 |
| 5 | M.2 | 150 | 0.123 |
| 6 | M.2 | 400 | 0.116 |
| 7 | M.2 | 600 | 0.111 |
| 8 | M.3 | 150 | 0.123 |

TABLE 6-continued

Boundary Friction Results

| Oil # | Molybdenum type | Amount of molybdenum in the finished oil (ppm Mo) | Boundary Friction Coefficient |
|---|---|---|---|
| 9 | M.3 | 400 | 0.118 |
| 10 | M.3 | 600 | 0.114 |

*Comparative example

It is clear from Table 6 that oils containing the molybdenum additives of the present invention (Oils#2–10) exhibit improved (i.e., reduced) boundary friction, which is indicative of improved fuel economy as described above, compared to the molybdenum-free lubricating oil.

This invention is susceptible to considerable variation in its practice. Accordingly, this invention is not limited to the specific exemplifications set forth hereinabove. Rather, this invention is within the spirit and scope of the appended claims, including the equivalents available as a matter of law.

The patentees do not intend to dedicate any disclosed embodiments to the public, and to the extent any disclosed modifications or alterations may not literally fall within the scope of the claims, they are considered to be part of the invention under the doctrine of equivalents.

What is claimed is:

1. An organic molybdenum complex comprising the reaction product of:
   (i) at least one long-chain monocarboxylic acid;
   (ii) at least one mono-alkylated alkylene diamine;
   (iii) glyceride(s); and
   (iv) an oxygen-containing molybdenum compound;
wherein said complex is substantially free of carbon disulfide.

2. The molybdenum complex of claim 1 wherein the long-chain monocarboxylic acid comprises a monocarboxylic acid containing at least 8 carbon atoms.

3. The molybdenum complex of claim 2 wherein the long-chain monocarboxylic acid comprises a monocarboxylic acid containing at least 12 carbon atoms.

4. The molybdenum complex of claim 2 wherein the long-chain monocarboxylic acid comprises a mixture of monocarboxylic acids.

5. The molybdenum complex of claim 3 wherein the long-chain monocarboxylic acid comprises oleic acid.

6. The molybdenum complex of claim 1 wherein the glyceride(s) comprises a mixture of mono-, di and triglycerides.

7. The molybdenum complex of claim 1 wherein the glyceride(s) comprises the reaction products of glycerol and oleic acid.

8. The molybdenum complex of claim 1 wherein from 30 to 70% of the available sites on the glycerides contain hydroxyl groups prior to forming said reaction product.

9. The molybdenum complex of claim 1 wherein the mono-alkylated alkylene diamine comprises a mono-alkylated alkylene diamine derived from a fatty acid.

10. The molybdenum complex of claim 9 wherein the mono-alkylated alkylene diamine derived from a fatty acid comprises at least one member selected from the group consisting of N-coco alkyl-1,3-propanediamine, N-tall oil alkyl-1,3-propanediamine and N-oleyl-1,3-propanediamine.

11. The molybdenum complex of claim 1 wherein the molybdenum source comprises at least one member selected from the group consisting of ammonium molybdate, sodium molybdate and molybdenum oxides.

12. The molybdenum complex of claim 1 obtained by reacting (i) and (ii) to form a reaction product prior to the addition of components (iii) and (iv).

13. The molybdenum complex of claim 12 wherein the reaction product comprises at least one member selected from the group consisting of aminoamides, ammonium carboxylate and mixtures thereof.

14. The molybdenum complex of claim 1 obtained by combining (i), (ii), (iii) and (iv) prior to heating.

15. The molybdenum complex of claim 1 wherein the reaction product has a ratio (wt/wt) of nitrogen to molybdenum (N/Mo) of $\leq 0.6$.

16. An organic molybdenum complex comprising the reaction product of:
   (i) at least one long-chain monocarboxylic acid;
   (ii) at least mono-alkylated alkylene diamine;
   (iii) glyceride(s); and
   (iv) a molybdenum source,
wherein the reaction product is substantially free of reactive sulfur.

17. The molybdenum complex of claim 15 wherein the reaction product has a N/Mo of $\leq 0.4$.

18. A molybdenum complex of claim 16 wherein said reaction product has a ratio (wt/wt) of nitrogen to molybdenum (N/Mo) of $\leq 0.4$.

19. The molybdenum complex of claim 17 wherein the reaction product has a N/Mo of $\leq 0.3$.

20. A molybdenum complex of claim 18 wherein said reaction product has a N/Mo of $\leq 0.3$.

21. The molybdenum complex of claim 1 wherein the reaction product is substantially free of reactive sulfur.

22. The molybdenum complex of claim 16 wherein said reaction product contains less than 0.05 weight percent of sulfur.

23. A lubricating oil composition comprising a major amount of an oil of lubricating viscosity and the molybdenum complex of claim 1.

24. The lubricating oil composition of claim 23 wherein the molybdenum complex is present in an amount sufficient to provide at least about 50 ppm of molybdenum to the finished lubricant.

25. A method of improving the oxidation stability of a lubricating oil comprising adding to said lubricating oil an oxidation stability improving amount of the molybdenum complex of claim 1, wherein said oxidation stability improving amount of said molybdenum complex is sufficient to improve the oxidative stability of the lubricating oil, as compared to the same lubricating oil except that it is devoid of said molybdenum complex.

26. The method of claim 25 wherein the molybdenum complex is present in the lubricating oil in an amount sufficient to provide at least 50 ppm of molybdenum to the finished lubricating oil.

27. A method of improving the fuel economy of an internal combustion engine comprising using as the crankcase lubricating oil for said internal combustion engine the lubricating oil of claim 23, wherein said molybdenum complex is present in an amount effective to improve the fuel economy of the internal combustion engine using said crankcase lubricating oil, as compared to said engine operated in the same manner and using the same crankcase lubricating oil except that the oil is devoid of said molybdenum complex.

28. The method of claim 27 wherein the molybdenum complex is present in said crankcase lubricating oil in an amount sufficient to provide at least 200 ppm of molybdenum to the finished lubricating oil.

29. A method of reducing deposits in an internal combustion engine comprising using as the crankcase lubricating oil for said internal combustion engine the lubricating oil of claim 23, wherein said molybdenum complex is present in an amount sufficient to reduce the weight of deposits in an internal combustion engine operated using said crankcase lubricating oil, as compared to the weight of deposits in said engine operated in the same manner and using the same crankcase lubricating oil except that the oil is devoid of said molybdenum complex.

30. The method of claim 29 wherein the molybdenum complex is present in said crankcase lubricating oil in an amount sufficient to provide at least 50 ppm of molybdenum to the finished lubricating oil.

31. A method of reducing wear in an internal combustion engine comprising using as the crankcase lubricating oil for said internal combustion engine the lubricating oil of claim 23, wherein said molybdenum complex is present in an amount sufficient to reduce the wear in an internal combustion engine operated using said crankcase lubricating oil, as compared to the wear in said engine operated in the same manner and using the same crankcase lubricating oil except that the oil is devoid of said molybdenum complex.

32. The method of claim 31 wherein the molybdenum complex is present in said crankcase lubricating oil in an amount sufficient to provide at least 50 ppm of molybdenum to the finished lubricating oil.

33. A process for preparing an organic molybdenum complex, said process comprises reacting:
  (i) at least one long-chain monocarboxylic acid;
  (ii) at least one mono-alkylated alkylene diamine;
  (iii) glyceride(s); and
  (iv) an oxygen-containing molybdenum compound;
wherein said complex is substantially free of carbon disulfide.

34. The process of claim 33 wherein the long-chain monocarboxylic acid comprises a monocarboxylic acid containing at least 8 carbon atoms.

35. The process of claim 34 wherein the long-chain monocarboxylic acid comprises a monocarboxylic acid containing at least 12 carbon atoms.

36. The process of claim 33 wherein the long-chain monocarboxylic acid comprises a mixture of monocarboxylic acids.

37. The process of claim 33 wherein the mono-alkylated alkylene diamine (component ii) is present in an amount of from 0.8 to 1.2 moles per mole of acid (component i).

38. The process of claim 33 wherein the glyceride(s) comprises a mixture of mono-, di and triglycerides.

39. The process of claim 33 wherein the glyceride(s) comprises the reaction products of glycerol and oleic acid.

40. The process of claim 33 wherein from 30 to 70% of the available sites on the glycerides contain hydroxyl groups prior to forming the molybdenum complex.

41. The process of claim 33 wherein the glyceride(s) (component iii) are present in an amount of from 0.25 to 0.75 mole per mole of acid (component i).

42. The process of claim 33 wherein the molybdenum source comprises at least one member selected from the group consisting of ammonium molybdate, sodium molybdate and molybdenum oxides.

43. The process of claim 33 wherein the molybdenum source (component iv) is present in an amount of from 0.5 to 1.5 moles per mole of acid (component i).

44. The process of claim 33 wherein components (i) and (ii) are reacted to form a reaction product prior to the addition of components (iii) and (iv).

45. The process of claim 44 wherein the reaction product comprises at least one member selected from the group consisting of aminoamides, ammonium carboxylate and mixtures thereof.

46. The process of claim 44 wherein water is added to the reaction mixture after the reaction of (i) and (ii).

47. The process of claim 46 wherein from 1 to 100 moles of water per mole of acid (component i) are added.

48. The process of claim 33 wherein components (i), (ii), (iii) and (iv) are combined prior to heating.

49. The process of claim 48 wherein from 1 to 100 moles of water per mole of acid (component i) are added to the reaction mixture of components (i), (ii), (iii) and (iv).

50. A process for preparing an organic molybdenum complex, said process comprises reacting:
  (i) at least one long-chain monocarboxylic acid;
  (ii) at least one mono-alkylated alkylene diamine;
  (iii) glyceride(s); and
  (iv) a molybdenum source;
wherein said reaction product is substantially free of reactive sulfur.

* * * * *